(12) United States Patent
Wolf et al.

(10) Patent No.: US 9,314,313 B2
(45) Date of Patent: Apr. 19, 2016

(54) ASYMMETRICAL SURGICAL WRIST REST

(76) Inventors: Benjamin Wolf, Madison, WI (US);
Jacob Wolf, Madison, WI (US);
Mitchell Wolf, Madison, WI (US);
Stephanie Wolf, Madison, WI (US)

( * ) Notice: Subject to any disclaimer, the term of this patent is extended or adjusted under 35 U.S.C. 154(b) by 632 days.

(21) Appl. No.: 13/274,768

(22) Filed: Oct. 17, 2011

(65) Prior Publication Data
US 2012/0097173 A1 Apr. 26, 2012

Related U.S. Application Data

(60) Provisional application No. 61/405,996, filed on Oct. 22, 2010.

(51) Int. Cl.
*A61G 13/12* (2006.01)
*A61B 19/00* (2006.01)

(52) U.S. Cl.
CPC ........................................ *A61B 19/28* (2013.01)

(58) Field of Classification Search
USPC .................. 128/845–846, 869–870, 877–879;
602/5, 20–23, 32, 36; 5/623–624,
5/646–647, 650–651, 601; 248/118.1,
248/118.3, 118.5
See application file for complete search history.

(56) References Cited

U.S. PATENT DOCUMENTS

| | | | | |
|---|---|---|---|---|
| 3,957,262 | A | * 5/1976 | McReynolds | ..................... 5/637 |
| 4,018,217 | A | * 4/1977 | Evans | ........................... 128/849 |
| 4,058,112 | A | 11/1977 | Johnson | |
| D264,875 | S | 6/1982 | Crocker | |
| 4,378,108 | A | 3/1983 | Bailey, Jr. | |
| 4,620,697 | A | 11/1986 | Pithon | |
| 4,655,293 | A | * 4/1987 | Criner et al. | ...................... 168/4 |
| 4,957,262 | A | 9/1990 | Kemper | |
| 6,076,208 | A | 6/2000 | Heimbrock et al. | |
| 6,108,840 | A | 8/2000 | Heimbrock et al. | |
| 6,374,439 | B2 | * 4/2002 | Heimbrock et al. | .............. 5/622 |
| 7,673,836 | B2 | 3/2010 | Wallock et al. | |
| 7,823,583 | B2 | 11/2010 | Allen et al. | |
| 7,823,843 | B2 | 11/2010 | Oberlaender et al. | |

FOREIGN PATENT DOCUMENTS

EP 0868885 A1 * 10/1998

OTHER PUBLICATIONS

Chan Wristrest, http://www.varitronics.com/vod_wristrest.htm.
Keeler Chan Wristrest, http://www.deviceoptical.com/pd_keeler_chan.cfm.
Galleano, et al., Can Armrests Improve Comfort and Task Performance in Laparoscopic Surgery?, *Annals of Surgery*, vol. 243, No. 3, pp. 329-333 (2006).

* cited by examiner

*Primary Examiner* — Ophelia A Hawthorne
(74) *Attorney, Agent, or Firm* — Daniel A. Blasiole; Joseph T. Leone, Esq.; DeWitt Ross & Stevens SC

(57) ABSTRACT

Wrist, hand, or arm support devices are provided. The support devices include a support member having a top surface and a front surface. The top surface is oriented at either a parallel angle or a non-parallel angle with respect to a work surface. The front surface curves upon itself to form either a symmetric or an asymmetric arc. Preferred versions of the support devices described herein include at least one of a top surface oriented at a non-parallel angle with respect to the work surface or a front surface that curves upon itself to define an asymmetric arc. Mounting members for connecting the support member to an operating surface are also provided. The support devices described herein permit an operator to comfortably rest his or her hand on the support devices while directing procedures toward non-centered portions of work objects.

20 Claims, 3 Drawing Sheets

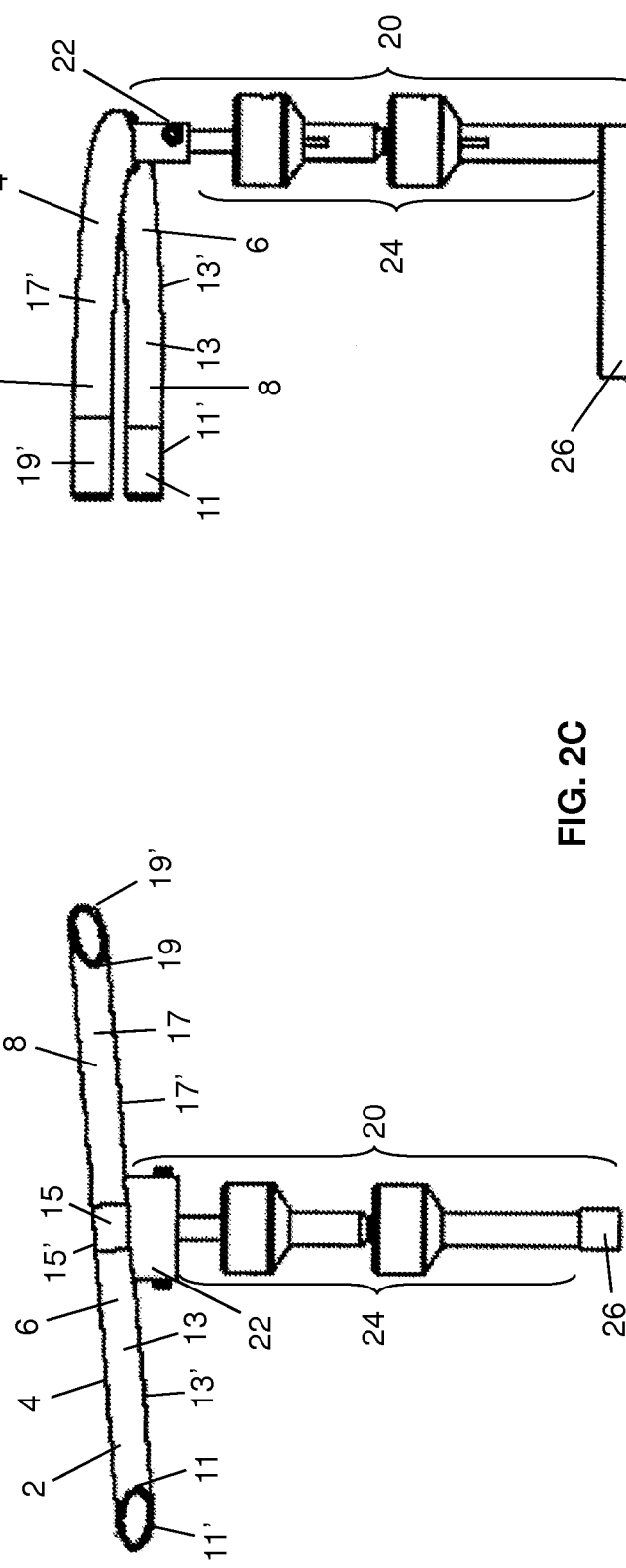
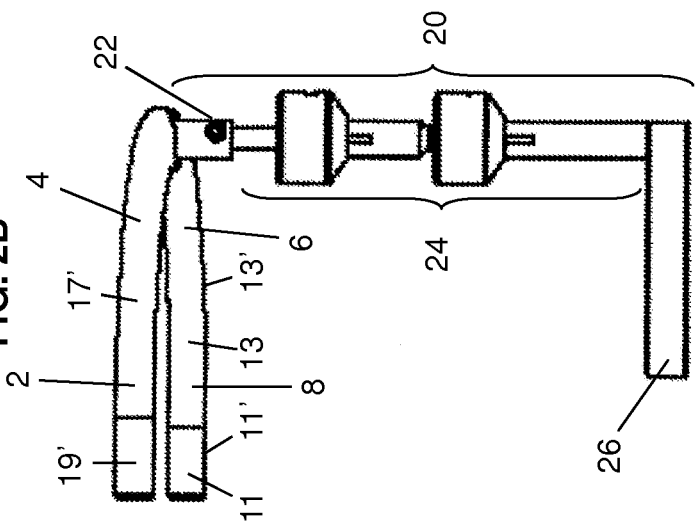
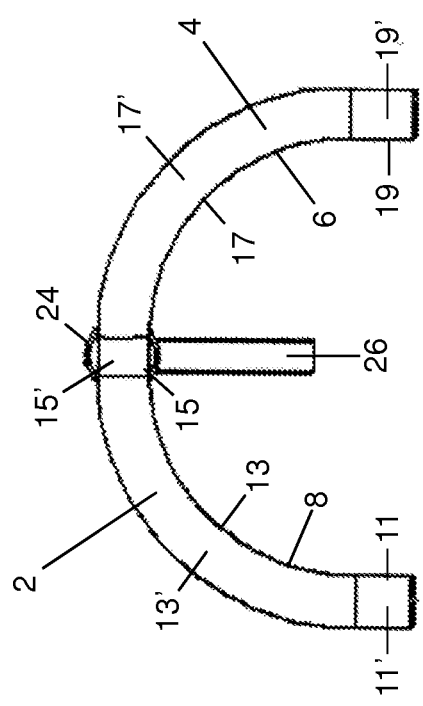

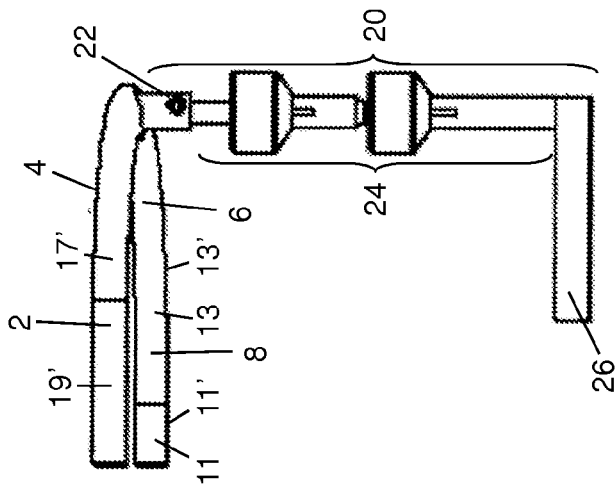
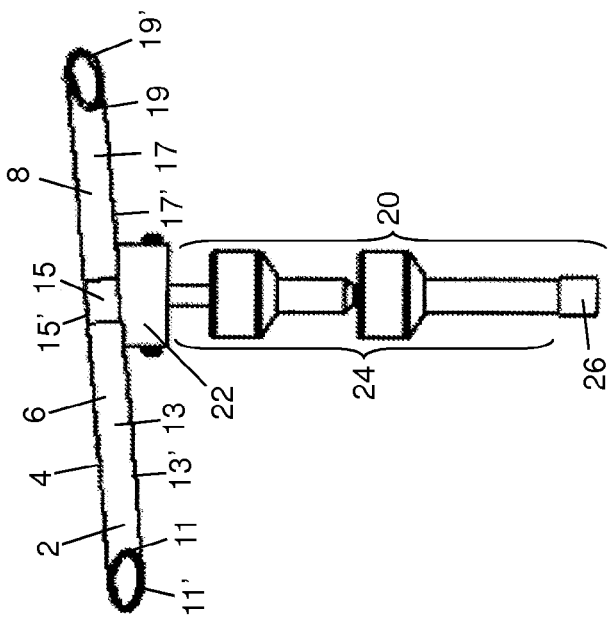
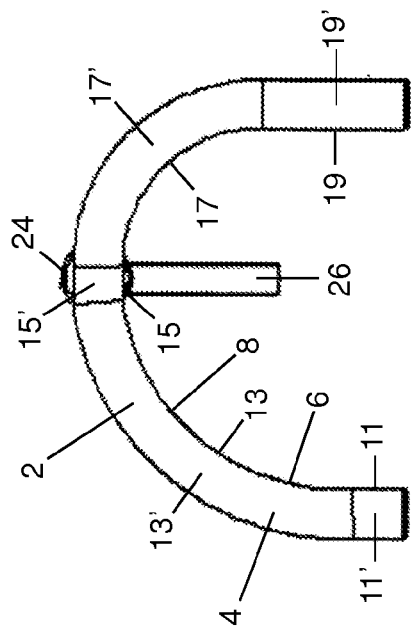

ASYMMETRICAL SURGICAL WRIST REST

CROSS-REFERENCE TO RELATED APPLICATIONS

This application claims priority under 35 USC §119(e) to U.S. Provisional Patent Application 61/405,996 filed Oct. 22, 2010, the entirety of which is incorporated herein by reference.

FIELD OF THE INVENTION

The invention is directed to devices for supporting an operator's hand, arm, or wrist while performing fine-tuned, delicate movements about a work object, such as performing surgery or similar operations on a head, neck, or eye of a patient.

BACKGROUND

When a physician performs eye surgery and similar delicate operations, it is important that the hand holding the scalpel or other instrument has a firm support throughout the operating procedure to permit small and precise movements. Various devices for supporting a surgeon's hand include support tables, arm rests, and wrist rests. See, e.g., U.S. Pat. Nos. 4,378,108; 4,018,217; and U.S. Design Pat. No. 264,875. Such devices are widely used in ophthalmic surgery, otolaryngology surgery, neurosurgery, etc. These support devices can also be used in performing other delicate operations, such as building small models, etc.

A conventional wrist rest most commonly used today is known as the Chan wrist rest. The Chan wrist rest consists of a curved, horseshoe-shaped bar that encircles a patient's head to support the surgeon's arms and wrists during, for example, ophthalmic surgery. The bar of the Chan wrist rest is both symmetrical in curvature and entirely disposed in a horizontal plane above the patient's head. In the case of eye surgery, this design presents a recurring problem in that either eye of the patient is off-center within the symmetric wrist rest. Regardless of which eye is being subject to surgery, the surgeon must often adopt uncomfortable and unsuitable wrist and hand positions to accomplish a given surgical maneuver. The alternative is to place the patient in an equally uncomfortable position to situate the eye to be operated upon in a suitable location where the surgeon can reach it comfortably.

There is a need for a support device that permits a surgeon or other operator to comfortably rest his or her hand on the support device while directing procedures to a non-centered portion of an object worked upon ("work object"), such as a patient's eye or side of the head.

SUMMARY OF THE INVENTION

The invention is directed to support devices that are purposefully asymmetrical or angled. The asymmetry or angularity provides comfortable access to non-centered portions of a work object.

A preferred support device of the present invention includes a support member having a top surface and a front surface, wherein the front surface defines a limit of extension of the top surface and thereby defines a limiting boundary of the top surface. The support device is configured with the top surface of the support oriented either at a parallel angle with respect to a work surface or at a non-parallel angle with respect to the work surface. The front surface preferably curves upon itself to form an arc. The arc formed by the front surface is either symmetric or asymmetric. Preferred versions of the support devices described herein include at least one of a top surface configured to be oriented at a non-parallel angle with respect to a work surface or a front surface that curves upon itself in an arc with a varying degree of curvature to define an asymmetric limiting boundary of the top surface.

In versions of the invention comprising an asymmetric arc, the arc may include a first curved portion with a first degree of curvature and a second curved portion with a second degree of curvature, wherein the first degree of curvature is greater than the second degree of curvature.

In some versions of the invention, the support member comprises a bar having a height, a width, and an extended length, wherein the bar curves upon itself along the length. In other versions of the invention, the support member comprises a platform such that the top surface comprises an extended, planar surface.

In some versions of the invention, the support member is rounded about its height and width such that the top surface is continuous with the front surface. In other versions of the invention, the top surface is separated from the front surface by a distinct interface.

The support device may further include a mounting member connected to the support member. The mounting members may be configured to orient the top surface of the support member either in parallel with an operating surface or at a non-parallel angle with respect to an operating surface.

Examples of mounting members include a mounting pivot, a mounting arm, and a base plate. The mounting pivot may enable pivoting of the support member from front to back, from side to side, or in all angles about the mounting pivot. The mounting arm may be an extendable mounting arm, a rotatable mounting arm, or both an extendable and rotatable mounting arm.

The support devices described herein permit an operator to comfortably rest his or her hand on the support devices while directing procedures toward non-centered portions of work objects.

The objects and advantages of the invention will appear more fully from the following detailed description of the invention in conjunction with the accompanying drawings.

BRIEF DESCRIPTION OF THE DRAWINGS

FIG. 2A depicts a front elevation view of a support device of the invention with a support member having a substantially symmetrical arc and configured to orient a top surface of the support member at a non-parallel angle with respect to an operating surface FIG. 2B depicts a side elevation view of the support device shown in FIG. 2A.

FIG. 2C depicts a top plan view of the support device shown in FIG. 2A.

FIG. 3A depicts a front elevation view of a support device of the invention with a support member having an asymmetrical arc and configured to orient a top surface of the support member at a non-parallel angle with respect to an operating surface.

FIG. 3B depicts a side elevation view of the support device shown in FIG. 3A.

FIG. 3C depicts a top plan view of the support device shown in FIG. 3A.

DETAILED DESCRIPTION OF THE INVENTION

Figure 1B:
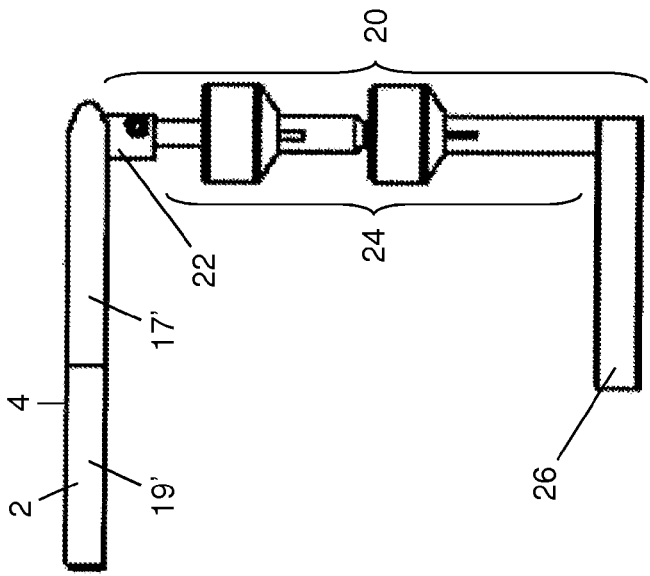
FIG. 1B depicts a side elevation view of the support device shown in FIG. 1A.

The support devices of the present invention include a support member 2, as shown in FIGS. 1A-3C. The term "support member" refers to any physical or extended object suitable for supporting a hand, arm, or wrist thereon. The support member 2 includes a top surface 4 and a front surface 6. The top surface 4 serves as an area of contact for the hand, arm, or wrist on the support member 2. Depending on the particular use, the top surface 4 may be flat, curved, angled, or contoured, and any angles, curvature, or contours may have consistent degrees of curvature or varying degrees of curvature. The front surface 6 defines a limit of extension of the top surface 4 and therefore defines a limiting boundary of the latter. As shown in the exemplary versions of the invention, the front surface 6 is substantially orthogonal or comprises at least a portion that is substantially orthogonal to the top surface 4.

In the exemplary versions of the invention shown in FIGS. 1A-3C, the support member 2 comprises a bar having a height, a width, and an extended length, wherein the bar is curved upon itself along the length. The bar is rounded about its height and width and has a top surface 4 that is continuous with the front surface 6. In addition, the width of the bar is greater than the bar's height, such that the bar comprises an oval or elliptical configuration. A width of about 2 inches or larger is preferred. This helps to provide a top surface 4 suitable for resting a hand, wrist, or arm thereon.

Other bar configurations are acceptable. For example, the bar may be substantially round, rather than oval or elliptical, such that its height is approximately equal to it width. Alternatively, the bar may have squared rather than rounded edges, such that the front surface 6 and the top surface 4 are mutually defined by a distinct interface, such as a sharp angle or corner. As with bars with rounded edges, bars with squared edges may have a width that is approximately equal to its height, or a width that is different with respect to its height. Preferred versions of bars with squared edges include a width that is greater than a height to provide a top surface 4 that is suitable for resting a hand, wrist, or arm thereon, as described above. Other desired regular or irregular bar shapes, e.g., compound curve, polygon, etc., are acceptable. For purposes of combining strength with light weight, the bars are preferably composed of hollow tubing.

In another version of the invention, the support member 2 comprises a platform or table rather than a bar, wherein the platform has an extended, planar top surface 4. As with the bar, the planar top surface 4 can be continuous with the front surface 6 by having a rounded edge between itself and the front surface 6 or can have a distinct interface formed by a sharp angle between itself and the front surface 6. In yet other versions of the invention, the support member 2 may comprise a block or any other extended object.

Regardless of the type of support member 2, the front surface 6 of the support member 2 is preferably configured to curve upon itself to form an arc 8. The arc 8 defined by the front surface 4 can embody any type of angle or curvature, such as sharp angles, rounded curvatures, or mixtures thereof, provided that the front surface 6 is at least partially disposed back toward itself. Various shapes that can be defined by the arc 8 include but are not limited to a "U"-shaped curvature (see FIG. 2C), a modified "U"-shaped curvature (see FIGS. 1C and 3C) or a bracket-shaped curvature (see U.S. Design Pat. No. 264,875). In the exemplary versions of the invention, the arc 8 includes a first end 11 and a second end 19 that are substantially parallel to each other and an internal portion 15 substantially orthogonal to the first 11 and second 19 ends. The arc 8 formed by the front surface 6 enables the support member 2 to be disposed around a patient's head and defines an access gap whereby a surgeon access portions of the patient's head or face during surgery.

In a version of the invention shown in FIGS. 2A-C, the arc 8 formed by the front surface 6 is symmetric. The arc 8 in this version has a first curved portion 13 between the internal portion 15 and the first end 11 and a second curved 17 portion between the internal portion 15 and the second end 19, wherein the first curved portion 13 and the second curved portion 17 comprise the same degree of curvature. A symmetric arc 8 can also be obtained by having straight lines and sharp angles at corresponding positions on either side of the internal portion 15. Any arc 8 configuration capable of providing symmetry is acceptable.

In versions of the invention shown in FIGS. 1A-C and 3A-C, the arc 8 formed by the front surface 6 is asymmetric. The arcs 8 in these versions are defined by the first curved portions 13 having a different degree of curvature than the second curved portions 17. To compensate for the different degrees in curvature, the first curved portion 13 is longer than the second curved portion 17, and the second end 19 of the arc 8 is longer than the first end 11 of the arc 8. Other ways of obtaining an asymmetric arc 8 are acceptable. For example, an asymmetric arc 8 can also be obtained by the support member 2 defining different types of curvature on either side of the support member 2, such as a continuous curve on one side of the internal portion 15 and a series of angles on the other. The asymmetric arc 8 is preferably configured to position each of the operator's hands equidistant from an off-centered portion of a work object, such as a patient's eye, rather than the midline of the work object, such as a patient's nose. Such asymmetry permits a surgeon or operator to comfortably rest his or her hand on the support device while directing procedures to a non-centered portion of a work object, such as an eye or a side of the head of a patient's body.

To suspend or stabilize the support member 2 in a suitable position for performing operations thereon, the support member 2 may be connected to one or more mounting members 20. The mounting members can take any form that stabilizes the support member in a position whereby the limiting boundary of the top surface 4 is disposed about an operating surface. As used herein, "operating surface" refers to any surface on which a work object is placed for a particular procedure requiring fine motor movements, such as surgery, to be performed. Non-limiting examples of operating surfaces include operating tables, stretchers, and other platforms. Non-limiting examples of mounting members 20 include mounting pivots 22, mounting arms 24, base plates 26, mounting brackets, mounting clamps, etc. Exemplary mounting pivots 22, mounting arms 24, and base plates 26 are shown in FIGS. 1A-3C. Each mounting member 20 can either be directly connected to the support member 2 or indirectly connected to the support member 2 via other mounting members 20.

In the exemplary versions of the invention, the mounting members 20 are connected to the support member 2 at a portion 15' of the support member 2 corresponding to the internal portion 15 of the arc 8. Such a connection is one of many suitable for enabling angling, pivoting, and rotating of the support member 2 in an efficient manner, as described further below. However, the mounting members 20 can be connected to any portion of the support member 2. For example, the mounting members 20 may also be connected to portions of the support member 2 corresponding to other portions of the arc 8, such as portions 11', 13', 17', and/or 19', which correspond to the first end 11, the first curved portion 13, the second curved portion 17, and the second end 19, respectively. The term "corresponding" used in the context of a particular portion of the support member 2 corresponding to a particular portion of the arc 8, refers portions of the support member 2 extending directly from that portion of the arc 8. Such corresponding positions or portions comprise the entire section of the support member 2, including as the top surface 4, the rear surface (opposite the front surface 6, not designated in the drawings), the bottom surface (opposite the top surface 4, not designated in the drawings), and any intervening portions.

The mounting member 2 can be configured to orient the top surface 4 of the support member 2 at one or more distinct orientations with respect to the operating surface. The orientation can either be fixed or adjustable.

Figure 1C:
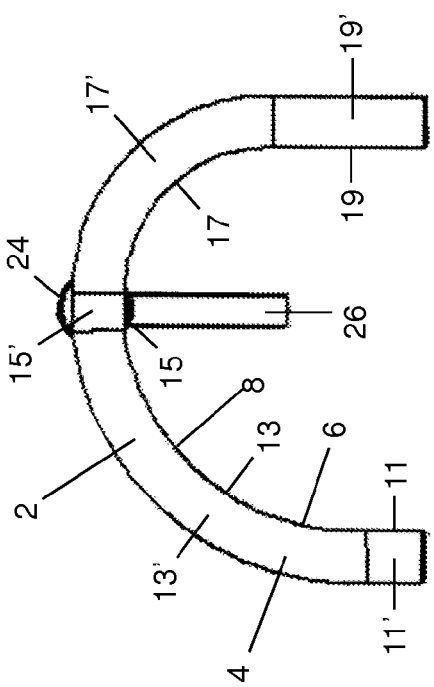
FIG. 1C depicts a top plan view of the support device shown in FIG. 1A.
Figure 1A:
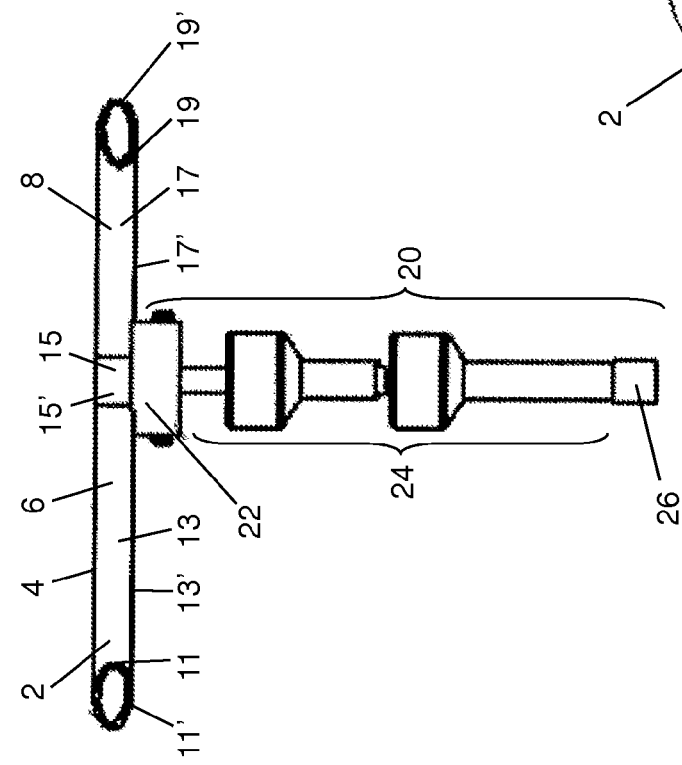
FIG. 1A depicts a front elevation view of a support device of the invention with a support member having an asymmetrical arc and configured to orient a top surface of the support member in parallel with an operating surface.

In the exemplary versions of the invention shown in FIGS. 1A-C, the mounting members 20 are configured to orient the top surface 4 of the support member 2 in parallel with an operating surface. As shown, the mounting members 20 include a mounting pivot 22 defining a horizontal plane connected to the support member 2 such that the top surface 4 is parallel to the horizontal plane, a mounting arm 24 defining a vertical axis connected to the support member 2 such that the top surface 4 is orthogonal to the axis, and a base plate 26 defining a horizontal plane connected to the support member 2 such that the top surface 4 is parallel to the horizontal plane. Such mounting members 20 and their connections render the top surface 4 of the support member 2 in parallel with the base plate 26. The base plate 26 can then be bolted to a surgical bed frame, placed under an operating room table pad, or otherwise mounted to or placed on the operating surface. Other ways of orienting the top surface 4 of the support member 2 in parallel with an operating surface are acceptable.

In the exemplary versions of the invention shown in FIGS. 2A, 2B, 3A, and 3B, the mounting members 20 are configured to orient the top surface 4 of the support member 20 at a non-parallel angle with respect to the operating surface. As used herein, "non-parallel angle" refers to any angle other than 0° and 180°. This is achieved in the exemplary versions by mounting the support member 2 on an angle-inducing mounting pivot 22, wherein the connection between the support member 2 and the mounting pivot 22 generates a non-parallel angle between the top surface 4 and a horizontal plane defined by the mounting pivot 22, a non-perpendicular angle between the top surface 4 and a vertical axis defined by the mounting arm 24, and a non-parallel angle between the top surface 4 and a horizontal plane defined by the base plate 26. Other ways of orienting the top surface 4 at a non-parallel angle with respect to the operating surface comprise providing an angle in one or more other mounting members 20, providing angles in the connections between the various mounting members 20, providing an angle in a connection between a mounting member 20 and the operating surface, and providing an angle in the top surface 4 itself. Another way if orienting the top surface 4 at a non-parallel angle with respect to the operating surface includes connecting mounting members 20 having or being adjustable to different lengths at various positions on the support member 2, e.g., at portions 11', 15', and 19'. The angle of the top surface 4 of the support member 2 with respect to the operating surface may comprise any angle between about 0.25° and 80°, more preferably between about 0.5° and 50°, and most preferably between about 1° and 45°. Examples include about 0.5°, about 1°, about 2.5°, about 5°, about 10°, about 15°, about 20°, about 25°, about 30°, about 35°, about 40°, or about 45°.

In the exemplary versions of the invention shown in FIGS. 2A, 2B, 3A, and 3B, the top surface 4 of the support member 2 is fixedly oriented in a "side-to-side" manner at a non-parallel angle with respect to the operating surface. Specifically, a portion 11' of the top surface 4 corresponding to the first end 11 of the arc 8 is disposed at a greater distance from the operating surface than the portion 19' of the top surface 4 corresponding to the second end 19 of the arc 8. In addition or alternatively, the support member 2 may be fixedly oriented in a "front-to-back" manner at a non-parallel angle with respect to the operating surface. For example, portions 11',19' of the top surface 4 corresponding to either or both of the first end 11 and second end 19 of the arc 8 may be disposed from the operating surface at a different distance than a portion 15' of the top surface 4 corresponding to the internal portion 15.

One or more of the mounting members 20 may be configured to permit the support member 2 to pivot, rotate, and/or raise and lower with respect to an operating surface on which it is mounted.

In exemplary versions of the invention in FIGS. 1A, 1B, 2A, 2B, 3A, and 3B, a pivotable support member 2 is shown. The support member 2 is capable of pivoting in a front-to-back manner by connecting a mounting pivot 22 to a position 15' on the support member 2 corresponding to the internal portion 15 of the arc 8. Such a configuration provides a fixed side-to-side orientation while permitting pivoting of the support member 2 from front-to-back. This arrangement provides for a stable, angled support that can be "lifted" out of the way during positioning of the work object. In other versions of the invention, the support member 2 can also be configured to pivot only side-to-side, both side-to-side and front-to-back, or in any degrees of pivotal freedom therebetween. The mounting pivot 22 may be freely pivotable. However, for the purpose of providing support at several distinct positions, it is preferable that the mounting pivot 22 is configured to be at least temporarily fixed at distinct orientations after being pivoted.

Versions of the invention comprising a height-adjustable (i.e., ability to raise or lower) support member 2 may be provided by connecting the support member 2 to one or more extendable mounting arms 24. One version of an extendable mounting arm 24 is one having a first end and a second end wherein the distance between the first end and second end is adjustable. The extendibility can be provided by a mechanism in which one end of the mounting arm 24 is capable of being inserted in the other at various positions and fixed in place with a screw. In another version of an extendable mounting arm 24, the mounting arm 24 has a fixed distance between its first end and its second end but is connected (directly or indirectly) at the first end to a support member 2 and connected at its second end to a clamp that permits the mounting arm 24 to adjustably slide therethrough. Alternatively, the mounting arm 24 can be connected to the support member 2 via the clamp at the first end of the mounting arm 24, and the second end can be fixedly connected to an object. In yet another configuration, both the support member 24 and the object can each be connected to the mounting arm 24 via a clamp. These configurations allow the effective length between an object and a support member 2 connected via a mounting arm 24 to be adjusted with the clamp.

In some versions of the invention, the support member 2 is capable of height adjustment and pivoting in all directions. This can be achieved by connecting the support member 2 to three mounting pivots at positions 11',19',15', corresponding to each of the first end 11 of the arc 8, the second end 19 of the arc 8, and the internal portion 15 of the arc 8. The mounting pivots in this version are preferably configured to provide pivoting freedom in all directions, such as occurs with a ball-and-socket joint. The mounting pivots 22 are then connected to height-adjustable mounting arms 24 that can be adjusted various lengths to orient the top surface at any desired orientation. In such a version, the support member 2 can be raised, lowered, pivoted from side-to-side, pivoted from front-to-back, or pivoted at any desired angle to permit a comfortable rest for a particular operator's needs.

Versions of the invention comprising a rotatable support member 2 may be provided by connecting the support member 2 to a rotatable mounting arm 24. A preferred rotatable mounting arm 24 comprises a first end and a second end, wherein the first end is rotatable with respect to the second end. The first end can be connected to the support member 2, and the second end can be connected to another object. The rotatable mounting arm 24 may be freely rotatable. However, for purposes of providing support in several distinct positions, it is preferable that the mounting arm 24 is configured to be fixed at distinct positions after being rotated. The rotatable mounting arm 24 can also be extendable as described above. An example of an extendable, rotatable mounting arm 24 is one can be inserted in the other, rotated with respect to the other at various positions, and fixed in place with a screw.

A rotatable mounting arm 24 can be connected either directly or indirectly to any portion of the support member 2 to permit rotation thereof. In the exemplary versions of the invention, the rotatable mounting arm 24 is connected via a mounting pivot 22 to a portion 15' of the support member 2 corresponding to the internal portion 15 of the arc 8. This configuration enables rotation of the support member 2 about the portion 15' of the support member 2 corresponding to the internal portion 15. The exemplary configuration provides for a stable, angled support that can be rotated out of the way during positioning of a work object.

The support member 2 and/or mounting members 20 can be made from any strong, solid material such as plastic or metal. Metal, such as steel or aluminum, is preferred. The support member 2 is preferably coated with a firm but resilient material such as polyurethane foam.

In some versions of the invention, several sizes of support members 2 may be provided wherein each size includes different degrees or shapes of curvature to fit different-sized hands. This is particularly preferred with support members 2 having an asymmetric arc 8. Each support member 2 may be able to be reversibly connected to the same mounting member 20 to accommodate many different operators. In one example, the support members 2 may be configured to fit three different hand sizes: a first configuration fitting hands corresponding to conventional glove sizes 6 and 6½, a second configuration fitting hands corresponding to conventional glove sizes 7 and 7½, and a third configuration fitting hands corresponding to conventional glove size 8. The support members 2 configured to fit smaller hands include arcs 8 with a sharper degree of curvature. The support members 2 configured to fit larger hands include arcs 8 with a lesser degree of curvature. The support members 2 configured to fit particular-sized hands are distinct from conventional wrist rests, wherein any curvature is configured to accommodate the shape of a patient's head rather than the size of the operator's hand.

In using the various support devices described herein, a work object is disposed on an operating surface with the support member at least partially surrounding the work object. An operator's hands can then rest on the support device while performing fine-tuned procedures on the work object. In the specific case of performing a surgery on a part of a patient's head, such as an eye, the support member 2 is suitably positioned about the patient's head such that the eye, rather than the head itself, is "centered" between the two ends 11',19'. In this fashion, the surgeon can reach the operative eye from a more natural, more comfortable, and more stable position.

The elements and steps described herein can be used in any combination whether explicitly described or not.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the following claims.

We claim:

1. A support device for a hand, wrist, or arm comprising:
   a support member that includes a top surface and a front surface, wherein the front surface defines a limit of extension of the top surface, wherein the front surface defines a concave, asymmetric arc with varying degree of curvature, and wherein:
   the arc comprises a first end, a first curved portion, an internal portion, a second curved portion, and a second end;
   the internal portion is disposed between the first curved portion and the second curved portion;
   the first curved portion is disposed between the internal portion and the first end;
   the second curved portion is disposed between the internal portion and the second end;
   the first end and the second end are substantially parallel to each other;
   the internal portion is substantially orthogonal to the first end and the second end; and
   a first portion of the arc spanning from the internal portion to the first end is asymmetric with respect to a second portion of the arc spanning from the internal portion to the second end, wherein the first curved portion defines a first degree of curvature, the second curved portion defines a second degree of curvature, and the first degree of curvature is greater than the second degree of curvature.

2. The support device of claim 1 further comprising at least one mounting member connected to the support member, wherein the mounting member comprises a mounting arm and a base plate, wherein the mounting arm is disposed between the support member and the base plate, and wherein the mounting member is configured to stably suspend the support member over the base plate in a first position with the top surface of the support member oriented at an angle of from about 0° to about 45° with respect to the base plate.

3. The support device of claim 2 wherein the mounting member is configured to stably suspend the support member over the base plate in the first position with the top surface of the support member oriented parallel to the base plate.

4. The support device of claim 3 wherein the mounting member is connected to the support member between the first end of the arc and the second end of the arc, wherein the mounting member further comprises a mounting pivot disposed between the mounting arm and the support member, and wherein the mounting pivot is configured to pivot the support member from the first position by simultaneously increasing a distance between the first end of the arc and the base plate and a distance between the second end of the arc and the base plate.

5. The support device of claim 4 wherein the pivot member is configured not to permit simultaneously increasing the distance between the first end of the arc and the base plate and decreasing the distance between the second end of the arc and the base plate.

6. The support device of claim 5 wherein the mounting arm is a rotatable mounting arm configured to permit rotation of the first and second ends of the arc about the internal portion, and wherein the mounting arm is an extendable mounting arm configured to increase a distance between the support member and the base plate.

7. The support device of claim 2 wherein the mounting member is configured to stably suspend the support member over the base plate in the first position with the top surface of the support member oriented non-parallel to the base plate at an angle between 0° and about 45° with respect to the base plate and with a first portion of the top surface corresponding to the first end of the arc being disposed at a greater distance from the base plate than a second portion of the top surface corresponding to the second end of the arc.

8. The support device of claim 7 wherein the mounting member is connected to the support member between the first end of the arc and the second end of the arc, wherein the mounting member further comprises a mounting pivot disposed between the mounting arm and the support member, and wherein the mounting pivot is configured to pivot the support member from the first position by simultaneously increasing a distance between the first end of the arc and the base plate and a distance between the second end of the arc and the base plate.

9. The support device of claim 8 wherein the pivot member is configured not to permit simultaneously increasing the distance between the first end of the arc and the base plate and decreasing the distance between the second end of the arc and the base plate.

10. The support device of claim 9 wherein the mounting arm is a rotatable mounting arm configured to permit rotation of the first and second ends of the arc about the internal portion, and wherein the mounting arm is an extendable mounting arm configured to increase a distance between the support member and the base plate.

11. The support device of claim 2 wherein the mounting member is connected to the support member between the first end of the arc and the second end of the arc and wherein the mounting member further comprises a mounting pivot disposed between the mounting arm and the support member.

12. The support device of claim 11 wherein the mounting pivot is configured to pivot the support member from the first position by simultaneously increasing a distance between the first end of the arc and the base plate and a distance between the second end of the arc and the base plate.

13. The support device of claim 12 wherein the pivot member is configured not to permit simultaneously increasing the distance between the first end of the arc and the base plate and decreasing the distance between the second end of the arc and the base plate.

14. The support device of claim 2 wherein the mounting arm is a rotatable mounting arm configured to permit rotation of the first and second ends of the arc about the internal portion.

15. The support device of claim 2 wherein the mounting arm is an extendable mounting arm configured to increase a distance between the support member and the base plate.

16. The support device of claim 1 wherein the support member comprises a bar having a height, a width, and an extended length, wherein the bar curves upon itself along the length.

17. The support device of claim 16 wherein the bar is rounded about the height and the width, and the top surface is continuous with the front surface.

18. The support device of claim 1 wherein the first curved portion consists of a substantially constant degree of curvature and the second curved portion consists of a substantially constant degree of curvature.

19. The support device of claim 18 wherein the first curved portion extends from the internal portion to the first end and the second curved portion extends from the internal portion to the second end.

20. The support device of claim 1 wherein the top surface comprises an extended, planar surface.

* * * * *